United States Patent
Nelms

(10) Patent No.: US 8,173,968 B1
(45) Date of Patent: May 8, 2012

(54) SYSTEM AND METHOD FOR IMPROVED RADIATION DOSIMETRY

(75) Inventor: Benjamin E Nelms, Merrimac, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/029,956

(22) Filed: Feb. 17, 2011

(51) Int. Cl.
*G01T 1/02* (2006.01)
(52) U.S. Cl. ................................. 250/370.07
(58) Field of Classification Search ............... 250/370.01–370.15; 378/97, 108
See application file for complete search history.

(56) References Cited

U.S. PATENT DOCUMENTS

| | | | |
|---|---|---|---|
| 4,538,071 A * | 8/1985 | Bardoux et al. | 250/505.1 |
| 6,974,254 B2 | 12/2005 | Paliwal et al. | |
| 7,371,007 B2 | 5/2008 | Nilsson | |
| 2004/0120560 A1 | 6/2004 | Robar et al. | |
| 2009/0242782 A1 | 10/2009 | Jursinic et al. | |
| 2009/0252292 A1 | 10/2009 | Simon et al. | |

OTHER PUBLICATIONS

Babic et al., "Three-dimensional dose verification for intensity-modulated radiation therapy in the radiological physics centre head-and-neck phantom using optical computed tomography scans of ferrous xylenol-orange gel dosimeters," 2008, International Journal of Radiation Oncology Biology Physics, vol. 70, No. 4, pp. 1281-1291.*

Van Esch et al; On-Line Quality Assurance of Rotational Radiotherapy Treatment Delivery by Means of a 2D Ion Chamber Array and the Octavius Phantom; Med. Phys. 34 (10), Oct. 2007; 2007 Am. Assoc. Phys. Med; pp. 3825-3837.

Commercially available Octavius Phantom Systems, as evidenced by: http://www.ptw.de/octavius.html, attached printouts created Jan. 20, 2011; 4 pages.

Jursinic et al; MapCHECK used for rotational IMRT measurements: Step-and-Shoot, Tomotherapy, RapidArc; Med. Phys. 37(6), Jun. 2010; pp. 2837-2846.

* cited by examiner

*Primary Examiner* — Kiho Kim
(74) *Attorney, Agent, or Firm* — Quarles & Brady LLP

(57) ABSTRACT

A radiation dosimetry quality assurance system is disclosed that includes a three-dimensional (3D) phantom extending along a longitudinal axis to form an exterior surface and an interior volume and a passage formed to extend into the interior volume of the 3D phantom to removeably receive a detector array therein. The system also includes an angular-compensation system coupled to the exterior surface of the 3D phantom and having a physical contour extending from the exterior surface of the 3D phantom and configured to control an angular dependence of the detector array during measurement of the actual radiation dose delivered by the radiation delivery system. The system further includes a detector-angle adjustment system configured to allow selection of a relative position of the detector array with respect to a radiation source of the radiation delivery system during measurement of the actual radiation dose delivered during the planned medical process.

17 Claims, 4 Drawing Sheets

SYSTEM AND METHOD FOR IMPROVED RADIATION DOSIMETRY

BACKGROUND OF THE INVENTION

The present invention relates to radiation systems and methods and, more particularly, relates to systems and methods for improved radiation dosimetry using a customizable three dimensional (3D) dosimetry phantom.

Radiation as a source for acquiring medical imaging data and delivering therapy has become a mainstay of modern medicine. In either clinical setting, but particularly radiation therapy, radiation is delivered to a defined target volume, generally a specifically designated portion of a patient. In radiation therapy, where the delivered dose is substantially higher than imaging applications, effort is made to deliver the radiation dose in such a manner that the healthy tissue surrounding the target tissues does not receive radiation doses in excess of desired tolerances. In order to achieve this control of the imparted dose to the subject, highly accurate radiation delivery techniques are required. Many factors provide difficulties in obtaining the desired level of accuracy, including differences between the planned and delivered dose distributions and uncertainty in subject position with respect to the treatment system.

Conventional external beam radiation therapy is commonly administered by directing a linear accelerator ("linac") to produce beams of ionizing radiation that irradiate the defined target volume in a patient. The radiation beam is a single beam of radiation that is delivered to the target region from several different directions, or beam paths. Together, the determination of how much dose to deliver along each of these beam paths constitutes the so-called radiation therapy "plan." The purpose of the treatment plan is to accurately identify and localize the target volume in the patient that is to be treated. This technique is well established and is generally quick and reliable.

Intensity modulated radiation therapy ("IMRT") is an external beam radiation therapy technique that utilizes computer planning software to produce a three-dimensional radiation dose map, specific to a target tumor's shape, location, and motion characteristics. IMRT treats a patient with multiple rays of radiation, each of which may be independently controlled in intensity and energy. Because of the high level of precision required for IMRT methods, detailed data must be gathered about tumor locations and their motion characteristics. In doing so, the radiation dose imparted to healthy tissue can be reduced while the dose imparted to the affected region, such as a tumor, can be increased. In order to achieve this, accurate geometric precision is required during the treatment planning stage. Thus, while conventional IMRT methods have had success in increasing the effective dose imparted to the defined target volume while mitigating the imparted radiation dose to the surrounding healthy tissue, further reduction of the radiobiological effect on healthy tissue is desirable.

Image-guided radiation therapy ("IGRT") employs medical imaging, such as computed tomography ("CT"), concurrently with the delivery of radiation to a subject undergoing treatment. In general, IGRT is employed to accurately direct radiation therapy using positional information from the medical images to supplement a prescribed radiation delivery plan. The advantage of using IGRT is twofold. First, it provides a means for improved accuracy of the radiation field placement. Second, it provides a method for reducing the dose imparted to healthy tissue during treatment. Moreover, the improved accuracy in the delivery of the radiation field allows for dose escalation in the tumor, while mitigating dose levels in the surrounding healthy tissue. The concern remains, however, that some high-dose treatments may be limited by the radiation toxicity capacity of healthy tissues that lay close to the target tumor volume.

However, despite the progressive sophistication in the systems methods for planning and delivering radiation therapy, there is still a substantial potential for the subject to receive undesired radiation doses. In particular, despite the ability to create complex treatment plans where 3D dose distributions are highly customized for each patient, there is a substantial potential for the actual dose delivered to be greater than the planned dose or to be received by the patient in a manner different than that simulated in the plan.

One reason for this undesired potential is a low availability/high cost of systems and methods to verify the radiation dose prior to or during the treatment. Another, more prevalent reason for this undesired potential is a substantial lack of systems and methods that allow for customized measurement and analysis of dose in critical regions of interest.

For example, many of the sophisticated radiation therapy modalities mentioned above feature rotational therapy where it is desirable to use a 3D phantom instead of the very common 2D arrays that are used for static gantry angle IMRT. However, such 3D phantoms generally fall into one of two categories: 3D phantoms coupled with 2D detection arrays and 3D phantoms coupled with 3D detection systems.

In a first case, some have attempted to employ commonly-available 2D radiation detection arrays inserted into fixed "3D" phantoms. In these cases, though the phantom extends along the three planes (sagittal, coronal, and transverse) corresponding to those planes of a subject, due to the use of a 2D detection array, these systems are only capable of measuring dose along the one plane along which the 2D detection array extends. Furthermore, these systems are plagued by inaccuracies associated with problems of angular dependence. That is, it is known that the 2D detection arrays have a substantial change in sensitivity with variations in the angle of incidence of radiation on the 2D detection array. Thus, the angular dependence of the 2D detection array limits the accuracy of these systems.

Some have recognized the limitations of these systems combining 3D phantoms with 2D detection arrays and, in a second case, have developed 3D dosimetry arrays that are combined with 3D phantoms in a fixed dose detector arrangement. However, these systems are expensive and have limited, if not entirely very unsuitable, detector placement. Thus, though such systems are quite sophisticated, they still present substantial limits on practical clinical use in per-patient dose quality assurance (QA).

It would therefore be desirable to provide a system and method for QA in radiation dosimetry that provides greater flexibility without increases in overall system costs or complexity.

SUMMARY OF THE INVENTION

The present invention overcomes the aforementioned drawbacks by providing a system and method for utilizing available detector arrays with a highly configurable 3D phantom to acquire accurate 3D dosimetry information. Specifically, the system and method allow user selection of a number of customizable features of the system based on a desired detector array to be used with the 3D phantom that both compensate for specific features of the desired detector array and allow the desired detector array to be utilized in a manner that improves the accuracy of the 3D dosimetry information, even when the desired detector array is a 2D detector array.

In accordance with one aspect of the invention, a radiation dosimetry quality assurance system is disclosed that is configured to measure an actual radiation dose delivered by a radiation delivery system during a planned medical process. The radiation dosimetry quality assurance system includes a three-dimensional (3D) phantom extending from a first end to a second end along a longitudinal axis to form an exterior surface and an interior volume and a passage formed to extend into the interior volume of the 3D phantom to removeably receive a detector array therein. The system also includes an angular-compensation system coupled to the exterior surface of the 3D phantom and having a physical contour extending from the exterior surface of the 3D phantom and configured to control an angular dependence of the detector array during measurement of the actual radiation dose delivered by the radiation delivery system during the planned medical process. The system further includes a detector-angle adjustment system configured to allow selection of a relative position of the detector array with respect to a radiation source of the radiation delivery system during measurement of the actual radiation dose delivered by the radiation delivery system during the planned medical process.

In accordance with another aspect of the invention, a radiation dosimetry quality assurance system is disclosed that is configured to measure an actual radiation dose delivered by a radiation delivery system during a planned medical process. The radiation dosimetry quality assurance system includes a three-dimensional (3D) phantom extending from a first end to a second end along a longitudinal axis to form an exterior surface and an interior volume and a passage formed to extend into the interior volume of the 3D phantom. An adapter system is configured to receive a detector array having a predetermined geometry and configured to removeably couple the detector array within the passage. The system also includes an angular-compensation system coupled to the exterior surface of the 3D phantom to control an angular dependence of the detector array during measurement of the actual radiation dose delivered by the radiation delivery system during the planned medical process. The system further includes a detector-angle adjustment system configured to allow selection of relative position(s) of the detector array with respect to radiation source(s) of the radiation delivery system during measurement of the actual radiation dose delivered by the radiation delivery system during the planned medical process and a processor configured to receive the measure of the actual radiation dose delivered by the radiation source during the planned medical process from the detector array and generate 3D dosimetry information therefrom.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
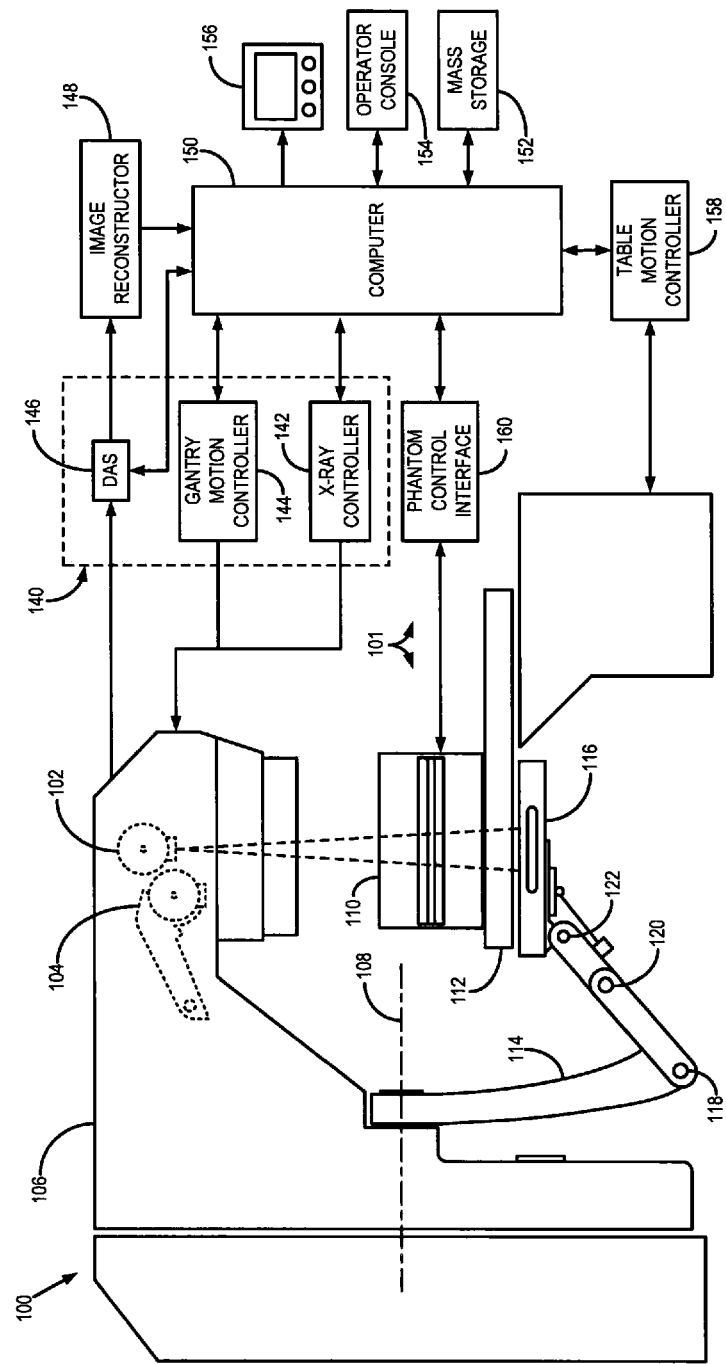
FIG. 1 is a block diagram of an exemplary image-guided radiation therapy ("IGRT") system and, associated therewith, a quality assurance dosimetry system in accordance with the present invention including customizable 3D dosimetry phantom.

Referring to FIG. 1, an exemplary image-guided radiation therapy (IGRT) system 100 is illustrated. The succeeding description of the invention is made with respect to the IGRT system 100; however, it should be readily appreciated by those skilled in the art that the present invention can be readily used with any number of radiation-delivery systems. For example, the present invention is readily designed for use with intensity modulated radiation therapy (IMRT) systems, stereotactic radiosurgery systems such as the CyberKnife® system (Accuray, Sunnyvale, Calif.), traditional gantry-mounted linear accelerator ("linac") systems, and other radiation-delivery and/or imaging systems that can benefit from the use of 3D dose measurement and quality assurance (QA) capabilities. Specifically, as will be described, the present invention provides a dosimetry quality assurance (QA) system 101 that can be configured and adapted for use with any of a variety of radiation sources and can be adjusted by clinicians to perform per-patient dose QA with an accuracy and cost efficiency generally unavailable from traditional systems.

The illustrated IGRT system includes a therapeutic x-ray source 102 and a diagnostic x-ray source 104. The diagnostic x-ray source 104 projects a cone-beam of x-rays toward a detector array 116. Both the therapeutic x-ray source 102 and diagnostic x-ray source 104 are attached adjacent each other and housed at the same end of a first rotatable gantry 106, which rotates about a pivot axis 108. The first rotatable gantry 106 allows either of the x-ray sources, 102 and 104, to be aligned in a desired manner with respect to the QA system 101 and, particularly, a configurable 3D phantom system 110 of the QA system 10 that is positioned on a patient table 112.

A second rotatable gantry 114 is rotatably attached to the first rotatable gantry 106 such that it too is able to rotate about the pivot axis, 108. Disposed on one end of the second rotatable gantry 114 is an x-ray detector 116. The x-ray detector 116 functions not only as a diagnostic image device when receiving x-rays from the diagnostic x-ray source 104, but also as a portal image device when receiving x-rays from the therapeutic x-ray source 102. The detector array 116 is formed by a number of detector elements that together sense the projected x-rays that pass through the subject 112. Each detector element produces an electrical signal that represents the intensity of an impinging x-ray beam and, hence, the attenuation of the beam as it passes through the subject 112. The second rotatable gantry 114 further includes an articulating end that can pivot about three points 118, 120, and 122. The pivoting motion provided by these points 118, 120, and 122, allows the x-ray detector 116 to be moved within a two-dimensional plane.

The rotation of the rotatable gantries, 106 and 114, and the operation of the x-ray sources, 102 and 104, are governed by a control mechanism 140 of the IGRT system 100. The control mechanism 140 includes an x-ray controller 142 that provides power and timing signals to the x-ray sources, 102 and 104, and a gantry motor controller 144 that controls the rotational speed and position of the gantries, 106 and 114. A data acquisition system ("DAS") 146 in the control mechanism 140 samples analog data from detector elements and converts the data to digital signals for subsequent processing. An image reconstructor 148, receives sampled and digitized x-ray data from the DAS 146 and performs high speed image reconstruction. The reconstructed image is applied as an input to a computer 150 which stores the image in a mass storage device 152.

The computer 150 also receives commands and scanning parameters from an operator via a console 154 that has a keyboard. An associated display 156 allows the operator to observe the reconstructed image and other data from the computer 150. The operator supplied commands and parameters are used by the computer 150 to provide control signals and information to the DAS 146, the x-ray controller 142 and the gantry motor controller 144. In addition, the computer 150 operates a table motor controller 158 which controls the motorized patient table 112 to position the subject 112 within the gantries, 106 and 114.

With the generalities of the IGRT system 100 serving as a general context for a radiation-delivery system, whether therapeutic or imaging, the present invention provides the aforementioned QA system 101. As will be described, the QA system 101 includes the configurable 3D phantom 110 and a phantom control interface 160 that connects the configurable 3D phantom 110 to the computer 150 of the IGRT system 100 or another computer system. As will be described, the configurable 3D phantom 110 and phantom control interface 160 are configured to operate in conjunction with a computer system to allow operators to select customizable dosimetry detection planes, control and compensate for angular dependence of detector accuracy, and translate feedback from a 2D detector array into a 3D dosimetry QA analysis.

Figure 2:
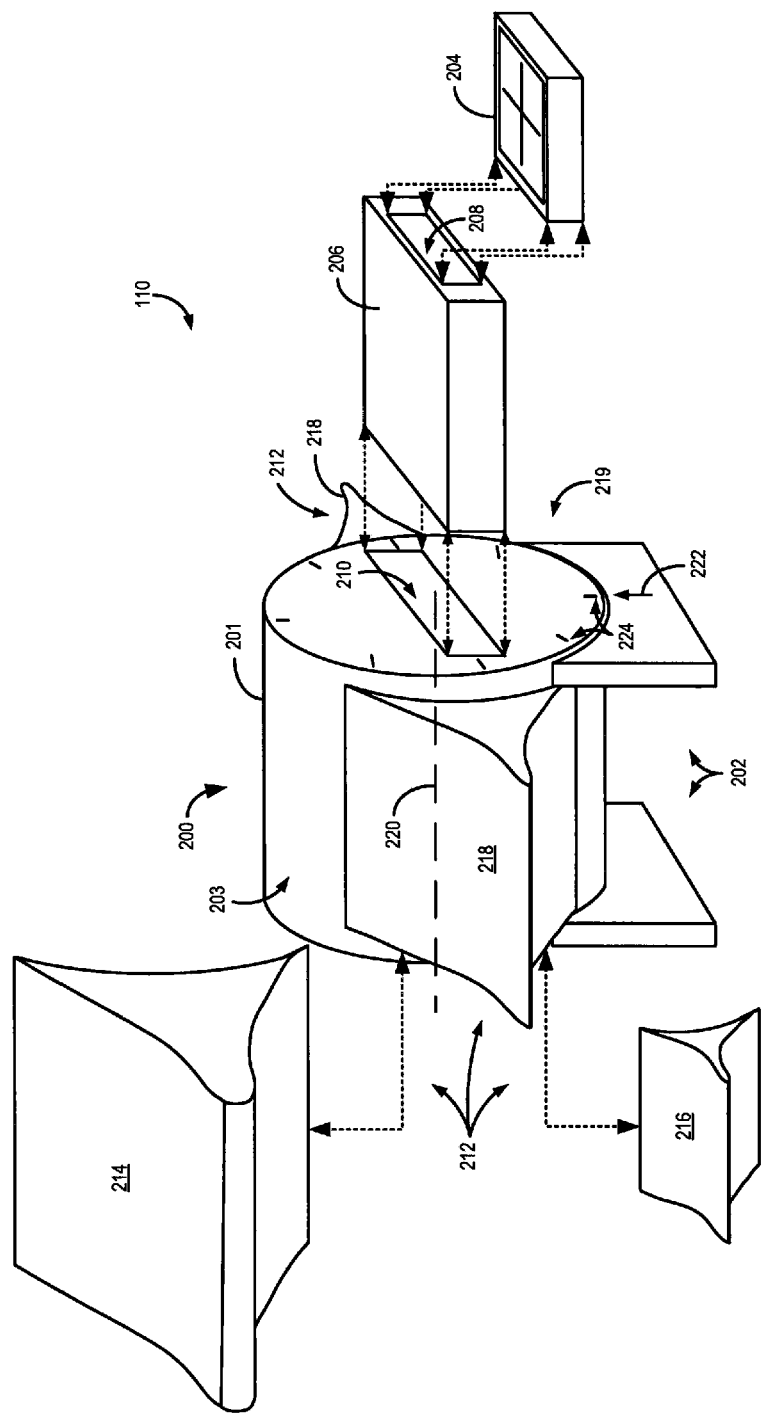
FIG. 2 is a perspective view of the customizable 3D dosimetry phantom of FIG. 1 in accordance with the present invention.
Figure 3:
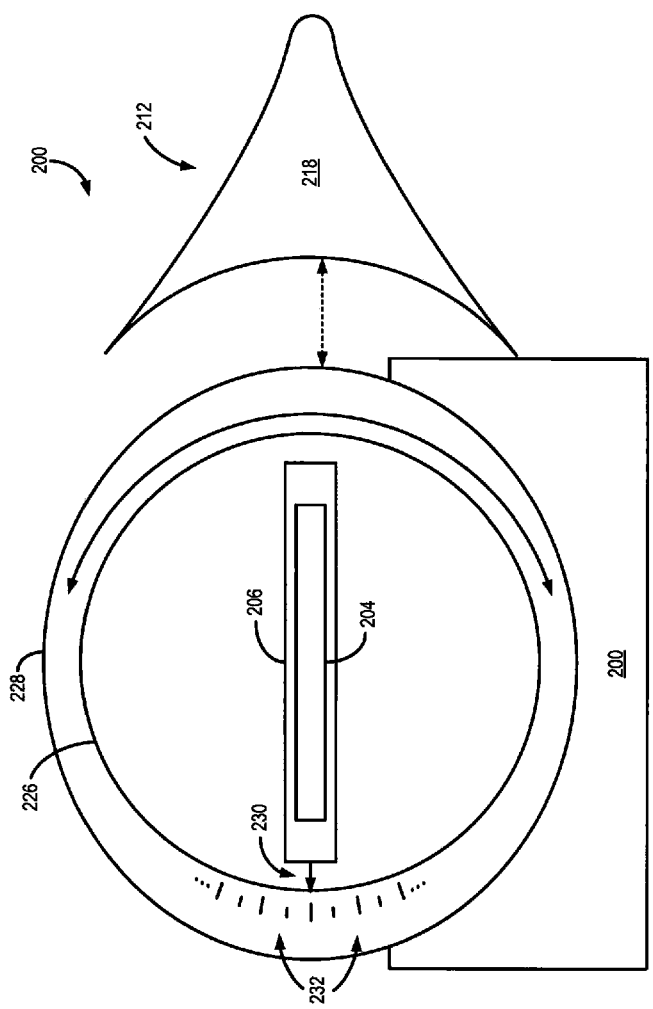
FIG. 3 is an elevational view of another configuration of the customizable 3D dosimetry phantom in accordance with the present invention.

Referring now to FIG. 2, the configurable 3D phantom system 110 of the present invention is illustrated in further detail. Specifically, the configurable 3D phantom system 110 includes a base phantom unit 200 that, as illustrated, may be formed as a cylinder or other shape, such as the oval-shaped cylinder of FIG. 3. Particularly when formed as a cylinder, the base phantom unit 200 may be accompanied by a rack or other support system 202 to allow the base phantom unit 200 to be advantageously positioned on the patient table of a radiation delivery system, such as illustrated in FIG. 1. However, as also illustrated in FIG. 3, the support system 202 may also be utilized with other advantageous shapes. Regardless of the particular shape of the base phantom unit 200, the 3D design of the base phantom unit 200 defines an exterior surface 201 and interior volume 203.

The base phantom unit 200 of the configurable 3D phantom system 110 is designed to receive any of a plethora of commercially-available 2D detector arrays 204. To facilitate coupling the variety of shapes, sizes, and designs of commercially-available 2D detector arrays 204, an adapter system 206 is provided. The adapter system 206 is formed by a plurality of interchangeable adapters having respective openings 208 configured to receive one of the commercially-available 2D detector arrays 204. Accordingly, regardless of the specific dimensions or configuration of a particular 2D detector array 204, a proper adapter system 106 can be used to couple the 2D detector array 204 with the base phantom unit 200 by positioning the particular 2D detector array 204 in the adapter system 206 through the opening 208 and positioning the combined 2D detector array 204 and adapter system 206 in a detector opening 210 formed in the base phantom unit 200. By providing a configurable 3D phantom system 110 that is capable of utilizing any of a variety of common 2D detector arrays 204, the configurable 3D phantom system 110 provides 3D QA capabilities at a fraction of the cost of dedicated 3D phantom systems having integrated 3D detector arrays. Furthermore, it provides the operator and maintenance staff with substantially greater flexibility and interoperability. Though illustrated as being designed to receive a 2D detector array 204 and 2D adapter system 206, it is contemplated that the base phantom unit 200 may include any of a variety of openings 210 configured to receive differing detector arrays 204 and associated adapter systems 206, including 3D detector geometries.

Beyond being customizable to receive any of a variety of detector arrays, the base phantom unit 200 may also include an angular-compensation system 212. The angular-compensation system 212 may be formed by a plurality of selected and, if desired, interchangeable angular dose-shaping wings 214, 216, 218. The dose-shaping wings 214, 216, 218 are designed to be coupled in pairs with the base phantom unit 200 to correct for the angular dependence of the particular detector array 214 that is coupled, through the adapter system 206, with the base phantom unit 200. Thus, preferably, the dose-shaping wings 214, 216, 218 are selected, along with the adapter system 206, based on the detector array 204 selected for coupling with the customizable 3D phantom system 110.

In addition to providing systems for correcting the angular dependence of a particular, selected detector array 204, the customizable 3D phantom system 110 includes a dynamically-adjustable, detector-angle system 219 designed to facilitate user-selection of optimized measurement planes within which to arrange the detector array 204. This is achieved by allowing user selection and adjustment of the relative position of the detector array 204 about a longitudinal axis 220 of the base phantom unit 200. As illustrated in FIG. 2, this user selection and adjustment can be achieved by rotating the base phantom unit 200 relative to the support system 202, such that the plane formed by the detector array 204 is rotated about a central axis formed by the longitudinal axis 220 of the base phantom unit 200. To assist in tracking the relative position of the measurement plane of the detector array 204 when being adjusted, it is contemplated that the support system 202 may include a reference indicator 222 configured to provide an indication of relative position relative to a plurality of angular markers 224 formed on the base phantom unit 200, or vice versa.

However, the configuration described with respect to FIG. 2 is but one system designed to facilitate user-selection of optimized measurement planes within which to arrange the detector array 204. For example, it is contemplated that the base phantom unit 200 may include an inner cylinder 226 configured to rotate within an outer shell 228. In this regard, it is contemplated that control and/or monitoring of the relative position of the detector array 204 may be performed automatically, for example, under computerized control. Whether or not automated, a positional indicator 230 and angular markers 232 may be provided, such as through indicators positioned on or about the inner cylinder 226 and outer shell 228.

Figure 4:
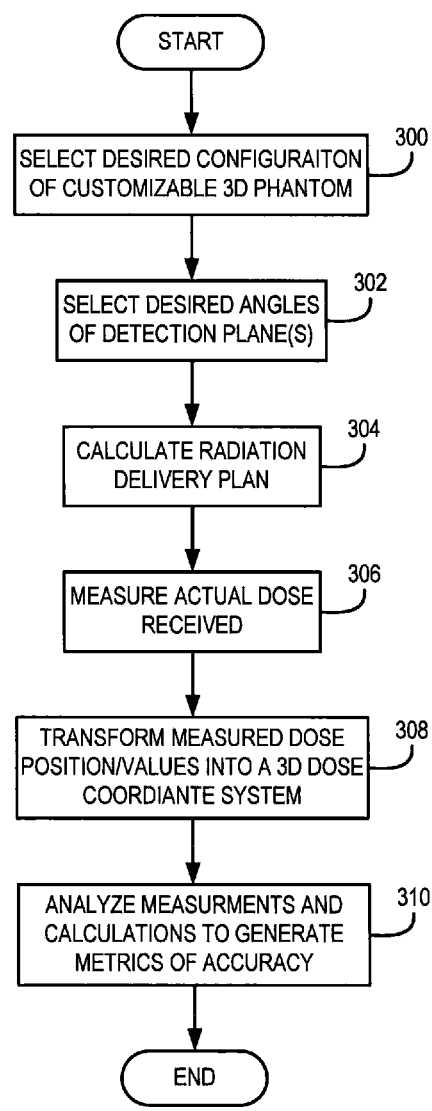
FIG. 4 is a flow chart setting forth the steps of a method for using the quality assurance dosimetry system in accordance with the present invention.

Referring now to FIG. 4, the general steps of a process for radiation delivery QA in accordance with the present invention are provided in a flow chart. The process begins at process block 300 by selecting a desired configuration of the above-described customizable 3D phantom. This step may take a variety of forms depending on the clinical setting and general resources available to the operator. For example, in some cases, the selection at process block 300 may be performed when purchasing the above-described customizable phantom. For example, during the purchasing of the QA system or the customizable 3D phantom, one may indicate the particular detector array intended for use with the QA system and the customizable 3D phantom. As such, the proper adapter and angular-compensation systems can be provided to couple the particular detector array with the customizable 3D phantom and compensate for the particular angular dependence of the selected detector array. Alternatively, of course, a plurality of adapter and angular-compensation systems may be readily available to the operator to then chose which adapter and angular-compensation systems to couple to the customizable 3D phantom based on the detector array.

Once the customizable 3D phantom has been properly coupled with a selected detector array and corresponding adapter and angular-compensation systems, at process block 302, the operator selects the desired angles for the detection plane based on the plan that will be evaluated using the QA system. As described above, this can be achieved by, for example, rotating the customizable 3D phantom in the support system or, if provided, by rotating an inner portion of the customizable 3D phantom within an outer portion of the customizable 3D phantom. In either case, the selection process performed in conjunction with process block 302 may be performed manually or with automated assistance, or may be performed in a fully automated fashion. In the manual case, the operator may rotate the detection plane as described above to a desired angle. In the case of automated assistance or a fully automated process, the computer and control systems associated with the QA system may suggest or automatically select a desired angle for the detection plane based on the specifics of the radiation delivery procedure that are planned.

Thereafter, at process block 304, the radiation delivery plan is calculated and, at process block 306, the actual dose received by the customizable 3D phantom is measured. Using the acquired measurements, at process block 308, an associated computer system transforms the measured dose positions/values into a 3D dose coordinate system matching what was previously calculated by the Treatment Planning System (TPS) in step 304. Thereafter, at process block 310, the measurements and calculations may be analyzed to generate metrics of accuracy pertaining to the radiation delivery plan.

Accordingly, a system and method are provided that permits user customizable angles of the dosimetry detection plane, physically controls the effects of angular dependence of detection arrays, and is capable of utilizing cost-effective and readily available 2D detector arrays and translating the acquired information into 3D information to thereby overcome the need to invest in costly, dedicated 3D detector arrays, unless desired. Unlike some traditional systems that provide multiple angles of the dosimetry detection plane by simply utilizing multiple detector arrays, for example in a "cross" configuration, the present invention provides the desired ability to use multiple angles of the dosimetry detection plane, without the cost associated with multiple, dedicated detector arrays in a fixed configuration. Similarly, while some systems may permit small ranges or fixed positions through which the angle of the dosimetry detection plane can be adjusted, the present invention provides a highly adjustable system that, for example, can provide an operator with a continuous range and continuously variable number of angles through which the dosimetry detection plane can be adjusted. Further still, many systems simply ignore the challenges of angular dependence of detector arrays and some systems have attempted to overcome these challenges by forming large, for example, cylindrical detector arrays or have included "shaping features," such as air pockets, within a 3D phantom, these attempts to overcome the challenges of angular dependence of detector arrays have substantial limitations. First, ignoring the challenges of angular dependence of detector arrays, particularly 2D detector arrays, reduces the effectiveness of any QA system and, in particular, seems to be counterproductive to an expressed goal of true quality assurance. Second, large, shaped, for example cylindrical, detector arrays are quite costly to manufacture and maintain. Finally, internally arranged, "shaping features," such as air pockets, limit the versatility of the 3D phantom substantially. For example, the necessary fixed position of the "shaping features" with respect to the detector array retrains the ability to perform any adjustment of the angle of the dosimetry detection plane. Similarly, these internal "shaping features" are designed very specifically to the particular angular dependence of the associated detector array and cannot be readily adjusted or reviewed/considered by the operator.

The present invention has been described in terms of one or more preferred embodiments, and it should be appreciated that many equivalents, alternatives, variations, and modifications, aside from those expressly stated, are possible and within the scope of the invention.

The invention claimed is:

1. A radiation dosimetry quality assurance system configured to measure an actual radiation dose delivered by a radiation delivery system during a planned medical process, the radiation dosimetry quality assurance system comprising:
   a three-dimensional (3D) phantom extending from a first end to a second end along a longitudinal axis to form an exterior surface and an interior volume;
   a passage formed to extend into the interior volume of the 3D phantom to removeably receive a detector array therein;
   an angular-compensation system coupled to the exterior surface of the 3D phantom and having a physical contour extending from the exterior surface of the 3D phantom and configured to control an angular dependence of the detector array during measurement of the actual radiation dose delivered by the radiation delivery system during the planned medical process; and
   a detector-angle adjustment system configured to allow selection of a relative position of the detector array with respect to a radiation source of the radiation delivery system during measurement of the actual radiation dose delivered by the radiation delivery system during the planned medical process.

2. The system of claim 1 further comprising an adapter system configured to be secured within the passage and configured to secure the detector array and respective dimensions within the passage to measure the actual radiation dose delivered by the radiation delivery system during the planned medical process.

3. The system of claim 1 wherein the passage is shaped to receive a two dimensional (2D) detector array and further comprising a computer system configured to be coupled to the 2D detector array to receive the measurement of the actual radiation dose delivered by the radiation delivery system during the planned medical process and extrapolate a 3D dosimetry information therefrom.

4. The system of claim 1 wherein the angular-compensation system includes a pair of angular dose-shaping wings configured to be coupled to the exterior surface of the 3D phantom in an opposing configuration proximate to the passage to compensate for angular dependence of the detector array when arranged in the passage.

5. The system of claim 4 further comprising a plurality of interchangeable angular dose-shaping wings having respective dose-shaping profiles, each specifically designed to compensate for a specific angular dependence of a particular detector array when arranged in the passage.

6. The system of claim 1 wherein the detector-angle adjustment system includes a support system configured to engage the 3D phantom and permit the 3D phantom and passage formed therein to be rotated within the support system to allow selection of the relative position of the detector array with respect to the radiation source of the radiation delivery system during measurement of the actual radiation dose delivered by the radiation delivery system during the planned medical process.

7. The system of claim 6 further comprising a plurality of markers and an indicator configured to provide an indication of a selected relative position of the detector array with respect to the radiation source of the radiation delivery.

8. The system of claim 1 wherein the 3D phantom includes an inner portion configured to rotate within an outer shell to form the detector-angle adjustment system and allow selection of the relative position of the detector array with respect to the radiation source of the radiation delivery system during measurement of the actual radiation dose delivered by the radiation delivery system during the planned medical process.

9. The system of claim 8 further comprising a plurality of markers and an indicator configured to provide an indication of a selected relative position of the detector array with respect to the radiation source of the radiation delivery.

10. A radiation dosimetry quality assurance system configured to measure an actual radiation dose delivered by a radiation delivery system during a planned medical process, the radiation dosimetry quality assurance system comprising:
   a three-dimensional (3D) phantom extending from a first end to a second end along a longitudinal axis to form an exterior surface and an interior volume;
   a passage formed to extend into the interior volume of the 3D phantom;
   an adapter system configured to receive a detector array having a predetermined geometry and configured to removeably couple the detector array within the passage;
   an angular-compensation system coupled to the exterior surface of the 3D phantom to control an angular dependence of the detector array during measurement of the actual radiation dose delivered by the radiation delivery system during the planned medical process;
   a detector-angle adjustment system configured to allow selection of a relative position of the detector array with respect to a radiation source of the radiation delivery system during measurement of the actual radiation dose delivered by the radiation delivery system during the planned medical process; and
   a processor configured to receive the measure of the actual radiation dose delivered by the radiation source during the planned medical process from the detector array and generate 3D dosimetry information therefrom.

11. The system of claim 10 wherein the detector array is a two-dimensional (2D) detector array and the processor is configured to extrapolate the 3D dosimetry information from 2D dosimetry information acquired by the 2D detector array.

12. The system of claim 10 wherein the angular-compensation system includes a pair of angular dose-shaping wings configured to be coupled to the exterior surface of the 3D phantom in an opposing configuration proximate to the passage to compensate for angular dependence of the detector array when arranged in the passage.

13. The system of claim 12 further comprising a plurality of interchangeable angular dose-shaping wings having respective dose-shaping profiles, each specifically designed to compensate for a specific angular dependence of a particular detector array when arranged in the passage.

14. The system of claim 10 wherein the detector-angle adjustment system includes a support system configured to engage the 3D phantom and permit the 3D phantom and passage formed therein to be rotated within the support system to allow selection of the relative position of the detector array with respect to the radiation source of the radiation delivery system during measurement of the actual radiation dose delivered by the radiation delivery system during the planned medical process.

15. The system of claim 14 further comprising a plurality of markers and an indicator configured to provide an indication of a selected relative position of the detector array with respect to the radiation source of the radiation delivery.

16. The system of claim 10 wherein the 3D phantom includes an inner portion configured to rotate within an outer shell to form the detector-angle adjustment system and allow selection of the relative position of the detector array with respect to the radiation source of the radiation delivery system during measurement of the actual radiation dose delivered by the radiation delivery system during the planned medical process.

17. The system of claim 16 further comprising a plurality of markers and an indicator configured to provide an indication of a selected relative position of the detector array with respect to the radiation source of the radiation delivery.

\* \* \* \* \*